(12) United States Patent
Fischer et al.

(10) Patent No.: US 6,169,198 B1
(45) Date of Patent: Jan. 2, 2001

(54) METHOD FOR PRODUCING MIXTURES OF MONOOLEFINIC $C_5$-MONONITRILES BY CATALYTIC HYDROCYANATION

(75) Inventors: Jakob Fischer, Kirchdorf; Wolfgang Siegel, Limburgerhof, both of (DE)

(73) Assignee: BASF Aktiengesellshaft, Ludwigshafen (DE)

( * ) Notice: Under 35 U.S.C. 154(b), the term of this patent shall be extended for 0 days.

(21) Appl. No.: 09/463,820

(22) PCT Filed: Aug. 4, 1998

(86) PCT No.: PCT/EP98/04851

§ 371 Date: Feb. 1, 2000

§ 102(e) Date: Feb. 1, 2000

(87) PCT Pub. No.: WO99/07671

PCT Pub. Date: Feb. 18, 1999

(30) Foreign Application Priority Data

Aug. 4, 1997 (DE) ............................................. 197 33 682

(51) Int. Cl.[7] .................................................. C07C 253/10
(52) U.S. Cl. ................................................................. 558/338
(58) Field of Search ............................................. 558/338

(56) References Cited

U.S. PATENT DOCUMENTS 4,714,773   12/1987   Rapoport .

FOREIGN PATENT DOCUMENTS

DW93313737   10/1993   (EP) .
DW94265899    8/1994   (EP) .
WO/9530680   11/1995   (WO) .

OTHER PUBLICATIONS

C.A. Tolman et al. "Catalytic Hydrocyanation of Olefin by Nickel (O) Phosphite Complexes–Effects of Lewis Acids" Organmetallics vol. 3, No. 1 (1984), pp. 33–38.

C.A. Tolman et al. "Homogenous Nickel–Catalyzed Olefin Hydrocyanation" Advances in Catalysis, vol. 33 (1985) pp. 1–46.

Kranenburg et al. "Effect of the Bite Angle of Diphosphine Ligands on Activigy and Selectivity in the Nickel–catalysed Hydrocyanation of Styrene" J. Chem. Soc., Chem Comm., (1995) pp. 2177–2178.

P.S. Elmes et al. "The Stereochemistry of Ogranometallic Compounds. XXI* Asymmetric Addition of Hydrogen Cyanide to Alkenes Catalysed by Zerovalent Metal Compounds" Aust. J. Chem., vol. 35, (1982) pp. 2041–2051.

T. Rajanbabu et al. "Role of Electronic Asymmetry in the Design of New Ligands: The Asymmetric Hydrocyanation Reaction" J.Am. Chem Soc., vol. 118, (1996) pp. 6325–6326.

K. Huthmacher et al. Reactions with Hydrogen Cyanide (Hydrocyanation), Applied Homogeneous Catalyst with Organometric Compounds, vol. 1, pp. 465–468;479 (1971).

Primary Examiner—Joseph K. McKane
Assistant Examiner—Ebenezer Sackey
(74) Attorney, Agent, or Firm—Keil & Weinkauf

(57) ABSTRACT

A process for preparing mixtures of monoolefinic $C_5$ mononitriles with nonconjugated C═C and C≡N bonds by catalytic hydrocyanation of 1,3-butadiene or a 1,3-butadiene-containing hydrocarbon mixture, wherein the hydrocyanation takes place in the presence of a catalyst which comprises at least one metallocene-phosphorus(III)-nickel(0) complex which comprises at least one monodentate or bidentate metallocene-phosphorus(III) ligand of the formula I

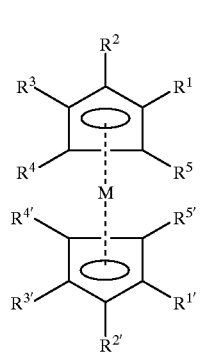

or salts and mixtures thereof.

23 Claims, No Drawings

METHOD FOR PRODUCING MIXTURES OF MONOOLEFINIC C₅-MONONITRILES BY CATALYTIC HYDROCYANATION

This Appln. is a 371 of PCT/EP 98/04851 filed Aug. 4, 1998.

The present invention relates to a process for preparing mixtures of monoolefinic $C_5$ mononitriles with nonconjugated C=C and C≡N bonds by catalytic hydrocyanation of a 1,3-butadiene-containing hydrocarbon mixture.

There is a great demand throughout the world for α,ω-alkylenediamines which are important starting materials in the industrial preparation of polyamides (nylons). The α,ω-alkylenediamines such as hexamethylenediamine are obtained almost exclusively by hydrogenation of the corresponding dinitriles. Virtually all industrial routes for preparing hexamethylenediamine are therefore essentially variants of the preparation of adiponitrile, about 1.0 million tons of which are produced around the world each year.

Four routes, which differ in principle, for preparing adiponitrile are described in K. Weissermel, H.-J. Arpe, Industrielle Organische Chemie, 4th edition, VCH Weinheim, pages 266 et seq.:

1. dehydrating amination of adipic acid with ammonia in the liquid or gas phase with intermediate formation of the diamide;
2. indirect hydrocyanation of 1,3-butadiene via intermediate 1,4-dichlorobutenes;
3. hydrodimerization of acrylonitrile in an electrochemical process, and
4. direct hydrocyanation of 1,3-butadiene with hydrogen cyanide.

In the last-mentioned process, monoaddition in a first stage results in a mixture of isomeric pentenonitriles, which is isomerized in a second stage mainly to 3- and 4-pentenonitriles. In a subsequent third stage, anti-Markownikoff addition of hydrogen cyanide onto 4-pentenonitrile results in adiponitrile. This reaction takes place in the liquid phase in a solvent such as tetrahydrofuran at a temperature in the range 30–150° C. under atmospheric pressure. The catalysts used for this are nickel complexes with phosphine or phosphite ligands and metal salt promoters. Complex phosphine ligands bound to metallocenes for stabilizing the nickel are not described in the abovementioned review.

There is a general description of the addition, with heterogeneous and homogeneous catalysis, of hydrogen cyanide onto olefins in Applied Homogeneous Catalysis with Organometalic Compounds, Vol. 1, VCH Weinheim, pages 465 et seq. The catalysts used for this are, in particular, based on phosphine and phosphite complexes, not bound to metallocenes, of nickel and palladium, which make high product selectivity, improved conversions and reduced reaction times possible. Adiponitrile is prepared by hydrocyanation of butadiene mainly using nickel(0) phosphite catalysts, in the presence or absence of a Lewis acid as promoter. The reaction can generally be divided into three steps:

1. synthesis of mononitriles by hydrocyanation of 1,3-butadiene;
2. isomerization; 3. synthesis of dinitriles. Formation of the monoadduct results in an isomer mixture composed of 3-pentenonitrile and 2-methyl-3-butenonitrile, and the selectivity for the linear 3-pentenonitrile is about 70% or less, depending on the catalyst used. If this first reaction step is carried out in the absence of Lewis acids, generally there is no second addition of hydrogen cyanide and the resulting product mixture can be subjected to an isomerization using the same catalyst systems as in the first reaction step, but this time in the presence or absence of a Lewis acid such as $ZnCl_2$ as promoter.

In this there is, on the one hand, isomerization of 2-methyl-3-butenonitrile to 3-pentenonitrile and, on the other hand, isomerization of 3-pentenonitrile to the various n-pentenonitriles. This publication mentions that the most thermodynamically stable isomer, 2-pentenonitrile in which the C,N triple bond is conjugated with the C,C double bond, inhibits the reaction because it acts as catalyst poison. The required isomerization to 4-pentenonitrile is made possible only because 3-pentenonitrile is isomerized considerably faster to 4-pentenonitrile than to 2-pentenonitrile.

The usual catalysts for the hydrocyanation of 1,3-butadiene are, in particular, the abovementioned nickel(0) phosphite catalysts with phosphite ligands without complex modification.

EP-A-0 274 401 describes a process for the hydrocyanation of pure butadiene using a nickel catalyst having a mixture of phenyl and m,p-tolyl phosphite ligands.

C. A. Tolman et al. describe, in Organometallics 3 (1984) 33 et seq., a catalytic hydrocyanation of olefins by nickel(0) phosphite complexes specifically taking account of the effects of Lewis acids on the addition of hydrogen cyanide.

In Advances in Catalysis, Volume 33, 1985, Academic Press, Inc., page 1 et seq. there is a review-like description of the homogeneous nickel-catalyzed hydrocyanation of olefins. This deals in particular with mechanistic aspects of the monohydrocyanation of butadiene to isomeric pentenonitriles, of the isomerization of 2-methyl-3-butenonitrile to 3-pentenonitrile and of the second addition of hydrogen cyanide to prepare adiponitrile. The catalysts employed are nickel (0) complexes, preferably with phosphite ligands.

Usual phosphines such as triphenylphosphine or 1,2-bis (diphenylphosphino)ethane have only low catalytic activity, if any, in the hydrocyanation of olefins.

WO 95/30680 describes bidentate phosphine chelate ligands in which the phosphine groups are bonded to aryl radicals which are fused by two bridges in ortho positions. In these, the first bridge comprises an O or S atom and the second bridge comprises an O, S or substituted N, Si or C atom. The two phosphine ligands are each located on a different aryl radical in the position ortho to the first bridge. These bidentate phosphine ligands are suitable, in the form of their transition metal complexes, as catalysts for hydroformylation, hydrogenation, polymerization, isomerization, carboxylation, crosscoupling, metathesis and hydrocyanation.

J. Chem. Soc., Chem. Commun. (1995) 2177 et seq. describes the effect of the bonding angle of the abovementioned bidentate phosphine ligands on the activity and selectivity in the nickel-catalyzed hydrocyanation of styrene.

None of the abovementioned publications describes a process for catalytic hydrocyanation using monodentate or polydentate nickel(0)-phosphorus(III) complexes in which the phosphorus(III) ligands in turn are covalently bonded to one or both of the cyclopentadienyl ligands of a metallocene.

EP-A 564 406 and EP-A 612 758 describe ferrocenyl-diphosphines as ligands for homogeneous catalysts and the use of these catalysts for enantioselective hydrogenation. In these ligands, two phosphine groups are bonded in the ortho position to the same cyclopentadienyl ligand of the ferrocene, one of them directly to the $C_5$ ring and the other via a substituted $C_1$-alkylene group. The rhodium and iridium complexes with these ligands are suitable as homogeneous enantioselective catalysts for hydrogenation of prochiral compounds with carbon or carbon/heteroatom double bonds. The use of these catalysts for hydrocyanation is not described.

Catalysts for asymmetric addition of hydrogen cyanide onto alkenes based on transition metal(0) complexes have been disclosed. Thus, Aust. J. Chem. 35 (1982) 2041 et seq. describes the use of [(+)-(diop)]$_2$Pd and [(+)-(diop)]$_2$Ni ((+)-(diop)=(+)-(2S,3S)-(2,3-isopropylidenedioxy-1,4-butanediyl)bis(diphenyl-phosphine)) as catalysts in enantioselective hydrocyanation.

J. Am. Chem. Soc. 118 (1996) 6325 et seq. describes the relationship of the electronic asymmetry of the ligands to the observed enantioselectivity in asymmetric hydrocyanation using electronically nonsymmetrical bis-3,4-diarylphosphonite ligands based on α-D-fructofuranosides.

It is an object of the present invention to provide a process for hydrocyanation in which the catalysts employed are to show high selectivity and good catalytic activity especially in the hydrocyanation of 1,3-butadiene-containing hydrocarbon mixtures to prepare mixtures of monoolefinic $C_5$-mononitriles with nonconjugated C=C and C≡N bonds and in the first and second addition of hydrogen cyanide to prepare adiponitrile.

We have found that this object is achieved by employing catalysts which comprise at least one metallocene-phosphorus(III)-nickel(0) complex.

The present invention thus relates to a process for preparing mixtures of monoolefinic $C_5$ mononitriles with nonconjugated C=C and C≡N bonds by catalytic hydrocyanation of 1,3-butadiene or a 1,3-butadiene-containing hydrocarbon mixture, wherein the hydrocyanation takes place in the presence of a catalyst which comprises at least one metallocene-phosphorus(III)-nickel(0) complex which comprises at least one monodentate or bidentate metallocene-phosphorus(III) ligand of the formula I

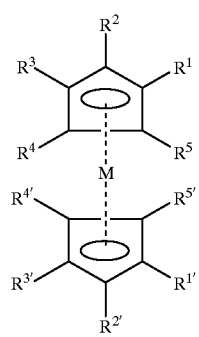

(I)

where $R^1$ is a radical of the formula $PL_2$ where the L radicals can be identical or different and are alkyl, cycloalkyl or aryl, $R^{1'}$ is hydrogen, alkyl or a radical of the formula $PL_2$ where the L radicals have the abovementioned meaning, $R^2, R^{2'}, R^3, R^{3'}, R^4, R^{4'}, R^5, R^{5'}$ are, independently of one another, selected from hydrogen, cycloalkyl, aryl or alkyl, which can be interrupted by an oxygen atom or substituted by a radical of the formula $NE^1E^2$ where $E^1$ and $E^2$ can be identical or different and are alkyl, cycloalkyl or aryl, or in each case two of the substituents $R^2, R^3, R^4, R^5$ and/or $R^{2'}, R^{3'}, R^{4'}, R^{5'}$ in adjacent positions can, together with the part of the cyclopentadienyl ring connecting them, be an aromatic or nonaromatic 5- to 7-membered carbocyclic or heterocyclic system which may have 1, 2 or 3 heteroatoms selected from O, N and S, M is Fe, Co, Ni, Ru, Os, Rh, Mn, Cr or V, or salts and mixtures thereof.

For the purpose of the present invention, the term 'alkyl' comprises straight-chain and branched alkyl groups. These are preferably straight-chain or branched $C_1$–$C_8$-alkyl, preferably $C_1$–$C_6$-alkyl, and particularly preferably $C_1$–$C_4$-alkyl, groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl , n-heptyl, 2-heptyl, 3-heptyl, 2-ethylpentyl, 1-propylbutyl and octyl.

The cycloalkyl group is preferably a $C_5$–$C_7$-cycloalkyl group such as cyclopentyl, cyclohexyl or cycloheptyl.

If the cycloalkyl group is substituted, it preferably has 1, 2, 3, 4 or 5, in particular 1, 2 or 3, alkyl radicals as substituents.

Aryl is preferably phenyl, tolyl, xylyl, mesityl or naphthyl and, in particular, phenyl.

Substituted aryl radicals have as substituents for example $C_1$–$C_8$-alkyl, $C_1$–$C_8$-alkoxy, halogen, trifluoromethyl, nitro or carboxyl. As a rule, 1, 2 or 3 substituents are preferred.

The L radicals in the $PL_2$ groups are different or, preferably, identical. Examples of suitable L radicals are $C_1$–$C_{12}$-alkyl and $C_5$–$C_{12}$-cycloalkyl, each of which can be substituted by one, two or three of the following groups: $C_1$–$C_4$-alkyl, $C_1$–$C_4$-alkoxy. Further examples of suitable L radicals are aryl which can be substituted by one, two or three of the following groups: $C_1$–$C_4$-alkyl, $C_1$–$C_4$-alkoxy, halogen, trifluoromethyl, sulfo, alkylsulfonyl, carboxyl, alkanoyloxy, alkoxycarbonyl, hydroxyl, nitro or cyano.

The L radicals are preferably phenyl.

If one of the radicals $R^2, R^{2'}, R^3, R^{3'}, R^4, R^{4'}, R^5$ or $R^{5'}$ is alkyl interrupted by an oxygen atom in ether linkage, possible examples thereof are 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-butoxybutyl and, preferably, 2-methoxyethyl.

If one of the radicals $R^2, R^{2'}, R^3, R^{3'}, R^4, R^{4'}, R^5$ or $R^{5'}$ is alkyl substituted by a radical of the formula $NE^1E^2$, possible examples are N,N-dimethylaminomethyl, N,N-dimethylaminoethyl, N,N-diethylaminomethyl, N,N-diethylaminoethyl or N,N-dimethylaminopropyl.

If in each case two of the substituents $R^2, R^3, R^4, R^5$ and/or $R^{2'}, R^{3'}, R^{4'}, R^{5'}$ in adjacent positions are, together with the part of the cyclopentadienyl ring connecting them, an aromatic or nonaromatic, 5- to 7-membered carbocyclic or heterocyclic system which additionally has 1, 2 or 3 heteroatoms selected from O, N and S, possible examples are indenyl, fluorenyl, azulenyl etc.

The two cyclopentadienyl rings in the metallocene-phosphorus(III) ligand of the formula I may be in the eclipsed or staggered conformation with various conformational angles. The planes of the cyclopentadienyl rings may be parallel or inclined toward one another, eg. depending on the central metal. The catalysts employed according to the invention comprise metallocene-phosphorus(III)-nickel(0) complexes having metallocene-phosphorus(III) ligands of the formula I having only one radical of the formula $PL_2$, b) bidentate metallocene-phosphorus(III) ligands of the formula I having two radicals of the formula $PL_2$ where the abovementioned structural circumstances of the ligand of the formula I make two-fold coordination of a transition metal possible, and c) bidentate or polydentate metallocene-phosphorus(III) ligands of the formula I, in which case one ligand coordinates different transition metals by different radicals of the formula $PL_2$, it being possible for chain-like metallocene-phosphorus(III)-nickel(0) complexes to result, eg. in a sandwich structure.

A zero valency transition metal may moreover coordinate one, two, three or four ligands of the formula I and, where appropriate, further ligands which are described hereinafter.

The central metal of the metallocene-phosphorus(III) ligand is preferably Fe.

In a suitable embodiment of the process according to the invention, the catalysts employed are those where $R^1$ is a radical of the formula $PL_2$ where the L radicals are phenyl, $R^{1'}$ is hydrogen or a radical of the formula $PL_2$ where the L radicals are, independently of one another, alkyl, cycloalkyl, substituted aryl and, in particular, phenyl, one of the substituents $R^2$, $R^{2'}$, $R^3$, $R^{3'}$, $R^4$, $R^{4'}$, $R^5$ or $R^{5'}$, preferably that in the position $\alpha$ to $R^1$ or $R^{1'}$, is hydrogen or alkyl which may be interrupted by an oxygen atom or substituted by a radical of the formula $NE^1E^2$ where $E^1$ and $E^2$ can be identical or different and are alkyl, and the other substituents $R^2$, $R^{2'}$, $R^3$, $R^{3'}$, $R^4$, $R^{4'}$, $R^5$, $R^{5'}$ are, independently of one another, hydrogen or methyl.

$R^{1'}$ is then preferably hydrogen or a radical of the formula $PL_2$ where the L radicals are isopropyl, cyclohexyl, trifluoromethyl-substituted phenyl or phenyl.

The catalysts according to the invention may, in addition to the metallocene-phosphine ligands of the formula I described above, additionally have at least one other ligand which is selected from halides, amines, carboxylates, acetylacetonate, aryl- or alkylsulfonates, hydride, CO, olefins, dienes, cycloolefins, nitrites, N-containing heterocycles, aromatic and heteroaromatic systems, ethers, $PF_3$ and monodentate, bidentate and polydentate phosphine, phosphinite, phosphonite and phosphite ligands, which is likewise monodentate, bidentate or polydentate and coordinates to the zero valency transition metal.

In a suitable embodiment of the process according to the invention, the catalysts employed comprise as metallocenephosphorus(III) ligand 1,1'-bis(diphenylphosphino)ferrocene,
1,1'-bis(dicyclohexylphosphino)ferrocene, or
1,1'-bis(diisopropylphosphino)ferrocene.

In a possible embodiment, the catalyst employed according to the invention comprises a chiral metallocenephosphine ligand of the formula I so that it is suitable for enantioselective catalysis. Enantioselective catalysis generally entails a compound which is already chiral or prochiral being reacted with use of the catalyst according to the invention, resulting in products with an enantiomeric excess or, preferably, enantiomerically pure products.

The catalysts according to the invention can be prepared by reacting at least one metallocene-phosphine ligand of the formula I and nickel powder or a nickel compound or a nickel complex in an inert solvent. Suitable nickel compounds in this connection are, for example, compounds in which the transition metal has an oxidation state higher than 0 and which are reduced in situ in the reaction with the metallocene-phosphorus(III) ligand of the formula I, in the presence or absence of a suitable reducing agent. These include, for example, the halides, preferably the chlorides, the acetates and the acetylacetonates of the abovementioned transition metals. Nickel(0) complexes are preferably prepared using $NiCl_2$. Examples of suitable reducing agents are alkali metals such as Na and K, and aluminum, and trialkylaluminum compounds.

If complex compounds of the transition metal are employed to prepare the metallocene-phosphorus(III)-nickel (0) complexes, the transition metal preferably has zero valency therein. Complexes with ligands which correspond to the abovementioned additional ligands in the complexes according to the invention are preferably employed for the preparation. In this case, preparation takes place by partial or complete ligand exchange with the metallocene-phosphorus (III) ligands of the formula I described above.

In a suitable embodiment of the process according to the invention, the nickel complex is bis(1,5-cyclo-octadiene) nickel(0).

Suitable inert solvents for preparing the metallocenephosphorus(III)-nickel(0) complexes are, for example, aromatic compounds such as benzene, toluene, ethylbenzene, chlorobenzene, ethers, preferably diethyl ether and tetrahydrofuran, or haloalkanes, for example dichloromethane, chloroform, dichloroethane and trichloroethane. The temperature in this case is in the range from −70° C. to 150° C., preferably from 0° C. to 100° C., particularly preferably at about room temperature.

Mixtures of monoolefinic $C_5$ mononitriles with nonconjugated C=C and C≡N bonds can be prepared by reacting a 1,3-butadiene-containing hydrocarbon mixture in the presence of one of the catalysts described above. This preferably results in mixtures with a high content of linear pentenonitriles.

Mixtures of monoolefinic $C_5$ mononitriles which contain, for example, 3-pentenonitrile and 2-methyl-3-butenonitrile, and which are suitable as intermediates for further processing to adiponitrile, can be prepared by employing pure butadiene or 1,3-butadiene-containing hydrocarbon mixtures.

If a hydrocarbon mixture is employed to prepare monoolefinic $C_5$ mononitriles by the process according to the invention, it preferably has a 1,3-butadiene content of at least 10% by volume, preferably at least 25% by volume, in particular at least 40% by volume.

1,3-Butadiene-containing hydrocarbon mixtures are obtainable on the industrial scale. Thus, for example, in petroleum processing the steam cracking of naphtha results in a hydrocarbon mixture which is called the $C_4$ cut and has a high total olefin content, about 40% comprising 1,3-butadiene and the remainder monoolefins and polyunsaturated hydrocarbons, plus alkanes. These streams always also contain small amounts, in general up to 5%, of alkynes, 1,2-dienes and vinylacetylene.

Pure 1,3-butadiene can be isolated, for example, by extractive distillation from industrial hydrocarbon mixtures. $C_4$ cuts are, where appropriate, essentially freed of alkynes, such as propyne or butyne, of 1,2-dienes such as propadiene, and of alkenynes such as vinylacetylene.

Otherwise, in some circumstances the resulting products have a C=C double bond in conjugation with the C≡N bond. It is disclosed in Applied Homogeneous Catalysis with Organometalic Compounds, Vol. 1, VCH Weinheim, page 479, that the conjugated 2-pentenonitrile which results from the isomerization of 2-methyl-3-butenonitrile and 3-pentenonitrile acts as inhibitor of the second addition of hydrogen cyanide to give adiponitrile. It has been found that the abovementioned conjugated nitriles obtained on hydrocyanation of a $C_4$ cut which has not been pretreated also act as catalyst poisons for the first reaction step in the preparation of adipic acid, the monoaddition of hydrogen cyanide.

This is why the components which constitute catalyst poisons in catalytic hydrocyanation, especially alkynes, 1,2-dienes and mixtures thereof, are partly or completely removed where appropriate from the hydrocarbon mixture. To remove these components, the $C_4$ cut is subjected, for the addition of hydrogen cyanide, to a partial catalytic hydrogenation. This partial hydrogenation takes place in the presence of a hydrogenation catalyst which is able to hydrogenate alkynes and 1,2-dienes selectively in the presence of other dienes and monoolefins.

Suitable heterogeneous catalyst systems for the selective hydrogenation generally comprise a transition metal compound, eg. on an inert carrier. Suitable inorganic carriers are the oxides usual for this purpose, especially silicas and aluminas, aluminosilicates, zeolites, carbides, nitrides etc. and mixtures thereof. Preferably used as carriers are $Al_2O_3$, $SiO_2$ and mixtures thereof. The heterogeneous catalysts used are particularly those described in U.S. Pat. No. 4,587,369; U.S. Pat. No. 4,704,492 and U.S. Pat. No. 4,493,906 which are incorporated herein by reference. Further suitable Cu-based catalyst systems are marketed by Dow Chemical as KLP catalyst.

Addition of hydrogen cyanide onto 1,3-butadiene or a 1,3-butadiene-containing hydrocarbon mixture, eg. a pretreated, partially hydrogenated $C_4$ cut, can take place continuously, semicontinuously or batchwise.

In a suitable variant of the process according to the invention, the addition of hydrogen cyanide takes place continuously. Reactors suitable for the continuous reaction are known to the skilled worker and are described, for example, in Ullmanns Enzyklopädie der technischen Chemie, Vol. 1, 3rd Edition, 1951, page 743 et seq. A cascade of stirred vessels or a tubular reactor is preferably used for the continuous variant of the process according to the invention.

In a preferred variant of the process according to the invention, the addition of hydrogen cyanide onto 1,3-butadiene or a 1,3-butadiene-containing hydrocarbon mixture takes place semicontinuously.

The semicontinuous process comprises:
a) charging a reactor with the hydrocarbon mixture, with or without part of the hydrogen cyanide and a hydrocyanation catalyst according to the invention which has been generated in situ where appropriate, with or without a solvent,
b) reacting the mixture at elevated temperature under elevated pressure, with hydrogen cyanide being fed in at the rate of its consumption in the semicontinuous procedure,
c) completing the conversion by subsequent reaction, followed by workup.

Suitable pressure-resistant reactors are known to the skilled worker and are described, for example, in Ullmanns Enzyklopädie der technischen Chemie, Vol. 1, 3rd Edition, 1951, page 769 et seq. An autoclave is generally used for the process according to the invention and can, if desired, be equipped with a stirring device and an inner lining. Account should preferably be taken of the following for the above steps:

Step a):

Before starting the reaction, the pressure-resistant reactor is charged with the partially hydrogenated $C_4$ cut, hydrogen cyanide, a hydrocyanation catalyst and, where appropriate, a solvent. Suitable solvents are those mentioned above for the preparation of the catalysts according to the invention, preferably aromatic hydrocarbons such as toluene, xylene or tetrahydrofuran.

Step b):

The mixture is generally reacted at elevated temperature under elevated pressure. The temperature is generally in the range from about 0 to 200° C., preferably about 50 to 150° C. The pressure is generally in the range from about 1 to 200 bar, preferably about 1 to 100 bar, in particular 1 to 50 bar, particularly preferably 1 to 20 bar. Hydrogen cyanide is fed in during the reaction at the rate at which it is consumed, keeping the pressure in the autoclave essentially constant. The reaction time is about 30 minutes to about 5 hours.

Step c):

To complete the conversion the reaction time can be followed by a period of from 0 minutes to about 5 hours, preferably about 1 hour to 3.5 hours, for subsequent reaction without hydrogen cyanide being fed into the autoclave. The temperature during this period is kept essentially constant at the reaction temperature previously set. Workup takes place by conventional processes and comprises removal of the unreacted 1,3-butadiene and unreacted hydrogen cyanide, eg. by washing or extraction, and distillation of the remaining reaction mixture to remove the required products and recover the still active catalyst.

In another suitable variant of the process according to the invention, the addition of hydrogen cyanide onto the 1,3-butadiene-containing hydrocarbon mixture takes place batchwise. The reaction conditions for this are essentially those described for the semicontinuous process but without additional hydrogen cyanide being fed in, but being completely present from the outset, in step b).

The preparation of adiponitrile from a butadiene-containing mixture by addition of 2 mole equivalents of hydrogen cyanide can generally be divided into three steps:

1. Preparation of $C_5$ monoolefin mixtures with nitrile functionality.
2. Isomerization of the 2-methyl-3-butenonitrile present in the mixtures to 3-pentenonitrile and isomerization of 3-pentenonitrile thus formed and present in the mixtures from step 1 to various n-pentenonitriles. This is intended to form a maximum content of 3-pentenonitrile and a minimum content of conjugated 2-pentenonitrile and 2-methyl-2-butenonitrile, which act as catalyst poison.
3. Preparation of adiponitrile by addition of hydrogen cyanide onto the 3-pentenonitrile which was formed in step 2 and which is previously isomerized in situ to 4-pentenonitrile. By-products of this are, for example, 2-methylglutaronitrile from Markownikoff addition of hydrogen cyanide onto 4-pentenonitrile or anti-Markownikoff addition of hydrogen cyanide onto 3-pentenonitrile, and ethylsuccinonitrile from Markownikoff addition of hydrogen cyanide onto 3-pentenonitrile.

The catalysts based on metallocene-phosphorus(III) ligands and employed according to the invention are also suitable and advantageous for the positional and double-bond isomerization in step 2 and the second addition of hydrogen cyanide in step 3.

In a preferred embodiment of the process according to the invention, the ratio of the amounts of 3-pentenonitrile to 2-methyl-3-butenonitrile obtained in the monoaddition of hydrogen cyanide onto the 1,3-butadiene-containing hydrocarbon mixture is at least 5:1, preferably at least 10:1, in particular at least 20:1. It is therefore generally possible to dispense with division of the process for preparing adiponitrile into the three steps of monoaddition of hydrogen cyanide onto a 1,3-butadiene-containing hydrocarbon mixture; isomerization; addition of hydrogen cyanide onto 4-pentenonitrile formed in situ; and the addition of 2 mole equivalents of hydrogen cyanide onto a 1,3-butadiene-containing hydrocarbon mixture can be designed as a one-stage process. The present invention therefore also relates to a process for preparing adiponitrile which comprises I) catalytic hydrocyanation of a mixture, which has been prepared as previously described, of $C_5$ mononitriles, where appropriate after further workup or isomerization, or II) catalytic hydrocyanation of a 1,3-butadiene-containing hydrocarbon mixture in a one-stage process, without workup and isomerization of $C_5$ mononitriles, in the presence of a catalyst of the formula I.

Not only do the catalysts employed according to the invention advantageously show high selectivity with regard to the monoaddition products obtained on hydrocyanation of 1,3-butadiene-containing hydrocarbon mixtures, but they can also be mixed with an excess of hydrogen cyanide for the hydrocyanation with negligible deposition of inactive nickel(II) compounds such as nickel(II) cyanide. In contrast to known hydrocyanation catalysts based on noncomplex phosphine and phosphite ligands, the catalysts of the formula I are thus suitable not only for continuous hydrocyanation processes in which an excess of hydrogen cyanide in the reaction mixture can generally be effectively avoided, but also for semicontinuous processes and batch processes in which, in general, a large excess of hydrogen cyanide is present. The catalysts employed according to the invention, and the hydrocyanation processes based thereon, thus generally display higher catalyst recycling rates and longer catalyst service lives than known processes. This not only improves the economics but is also ecologically advantageous because the nickel cyanide formed from the active catalyst with hydrogen cyanide is highly toxic and must be worked up or disposed of at high cost.

Besides hydrocyanation of 1,3-butadiene-containing hydrocarbon mixtures, the catalysts of the formula I are generally suitable for all conventional hydrocyanation processes. Those which may be particularly mentioned are the hydrocyanation of styrene and of 3-pentenonitrile.

The catalysts described above can also be employed for isomerizing 2-methyl-3-butenonitrile to 3-pentenonitrile. Catalysts which comprise chiral metallocene-phosphorus (III) ligands of the formula I are suitable for enantioselective hydrocyanation.

The invention is illustrated in detail by the following, non-limiting examples.

EXAMPLES

Example 1 (according to the invention)

Hydrocyanation of 1,3-butadiene 0.82 g of bis(1,5-cyclooctadiene)nickel(0), 3.32 g of 1,1'-bis(diphenylphosphino)ferrocene and 10 ml of toluene are mixed together in a glass autoclave at room temperature under argon, the reaction mixture immediately becoming reddish brown. After about 1 hour, a mixture of 16.2 g of 1,3-butadiene and 40 g of toluene is added. The glass autoclave is tightly closed and the mixture is heated to 90° C., an initial pressure of 3.4 bar being set up. The temperature is kept constant at 90° C., and a mixture of 4.0 g of freshly distilled hydrocyanic acid and 30 ml of toluene is metered in continuously, over a period of 80 minutes. The pressure has fallen to 1.4 bar after this. The reaction is then completed by subsequent reaction at 90° C. for 110 minutes. Toluene is used to rinse out the reactor. The progress of the reaction is followed by measuring the pressure and temperature.

In a subsequent Volhard cyanide determination, no cyanide is detected, and thus there has been virtually complete conversion of hydrogen cyanide.

GC analysis (column: 30 m stable wax, temperature program: 5 minutes isothermal at 50° C., subsequent heating to 240° C. at 5° C./min, gas chromatograph: Hewlett Packard HP-5890) with internal standard (benzonitrile): 75% of 3-pentenonitrile and 2-methyl-3-butenonitrile based on hydrogen cyanide.

3-Pentenonitrile: 2-methyl-3-butenonitrile ratio= 30:1.

Example 2 (according to the invention)

Hydrocyanation of 1,3-butadiene 0.14 g of bis(1,5-cyclooctadiene)nickel(0), 1.65 g of 1,1'-bis(diphenylphosphino)ferrocene and 10 ml of toluene are mixed together in a glass autoclave at room temperature under argon, the reaction mixture immediately becoming reddish brown. After about 1 hour, a mixture of 16.2 g of 1,3-butadiene and 40 g of toluene is added. The glass autoclave is tightly closed and the mixture is heated to 80° C., an initial pressure of 3.4 bar being set up. The temperature is kept constant at 80° C., and a mixture of 4.0 g of freshly distilled hydrocyanic acid and 30 ml of toluene is metered in continuously, over a period of 90 minutes. The pressure has fallen to 2.0 bar after this. The reaction is then completed by subsequent reaction at 80° C. for 60 minutes. Toluene is used to rinse out the reactor. The progress of the reaction is followed by measuring the pressure and temperature In a subsequent Volhard cyanide determination, 0.004% by weight, based on 120.1 g, of cyanide is found. The hydrogen cyanide conversion is thus 99.5%.

GC analysis (column: 30 m stable wax, temperature program: 5 minutes isothermal at 50° C., subsequent heating to 240° C. at 5° C./min, gas chromatograph: Hewlett Packard HP-5890) with internal standard (benzonitrile): 81.7% of 3-pentenonitrile and 2-methyl-3-butenonitrile based on hydrogen cyanide.

3-Pentenonitrile: 2-methyl-3-butenonitrile ratio=
30:1.

Example 3 (according to the invention)

Hydrocyanation of C₄ cut

TABLE 1

Composition of the Chd 4 cut

| Compound | % by vol |
|---|---|
| 1,3-Butadiene | 40.50 |
| cis-2-Butene | 2.65 |
| trans-2-Butene | 4.30 |
| Isobutene | 30.20 |
| 1-Butene | 14.30 |
| Isobutane | 1.10 |
| n-Butane | 2.90 |
| Propyne | 0.50 |
| Carbon dioxide | 0.10 |
| Vinylacetylene | 0.35 |

0.41 g of bis(1,5-cyclooctadiene)nickel(0), 0.80 g of 1,1'-bis(diphenylphosphino)ferrocene and 10 ml of toluene are mixed together in a glass autoclave at room temperature under argon, the reaction mixture immediately becoming reddish brown. After about 1 hour, a mixture of 39 g of C₄ cut with a composition shown in Table 1 and 50 g of toluene is added. The glass autoclave is tightly closed and the mixture is heated to 80° C., an initial pressure of 3.9 bar being set up. The temperature is kept constant at 80° C., and a mixture of 4.0 g of freshly distilled hydrocyanic acid and 30 ml of toluene is metered in continuously, over a period of 120 minutes. The pressure has fallen to 2.5 bar after this. The reaction is then completed by subsequent reaction at 80° C. for 120 minutes. Toluene is used to rinse out the reactor. The progress of the reaction is followed by measuring the pressure and temperature.

In a subsequent Volhard cyanide determination, 0.01%, based on 134.1 g, of cyanide is found. The hydrogen cyanide conversion is thus 99.9%.

GC analysis (column: 30 m stable wax, temperature program: 5 minutes isothermal at 50° C., subsequent heating to 240° C. at 5° C./min, gas chromatograph: Hewlett Packard HP-5890) with internal standard (benzonitrile): 84.7% of 3-pentenonitrile and 2-methyl-3-butenonitrile based on hydrogen cyanide.

3-Pentenonitrile: 2-methyl-3-butenonitrile ratio=
23.8:1.

Example 4 (comparative)

Hydrocyanation with triphenylphosphine-based catalyst 6.0 g of toluene, 0.1 g of bis(1,5-cyclooctadiene)nickel(0) and 0.39 g of triphenylphosphine are mixed together in a glass miniautoclave under argon at room temperature. After about 1 hour, first 2.0 g of 1,3-butadiene and then 1.0 g of freshly distilled hydrocyanic acid are added. The glass autoclave is tightly closed and the mixture is maintained at 80° C. under autogenous pressure. After reaction for 5 hours, the mixture is allowed to cool and then analyzed.

GC analysis (column: 30 m stable wax, temperature program: 5 minutes isothermal at 50° C., subsequent heating to 240° C. at 5° C./min, gas chromatograph: Hewlett Packard HP-5890) with internal standard (benzonitrile): 5.7% of 3-pentenonitrile and 2-butenonitrile based on hydrogen cyanide.

3-Pentenonitrile: 2-methyl-3-butenonitrile ratio=
0.91:1.

We claim:
1. A process for preparing mixtures of monoolefinic C₅ mononitriles with nonconjugated C=C and C≡N bonds by catalytic hydrocyanation of 1,3-butadiene or a 1,3-butadiene-containing hydrocarbon mixture, wherein the hydrocyanation takes place in the presence of a catalyst which comprises at least one metallocene-phosphorus(III)-nickel(0) complex which comprises at least one monodentate or bidentate metallocene-phosphorus(III) ligand of the formula I

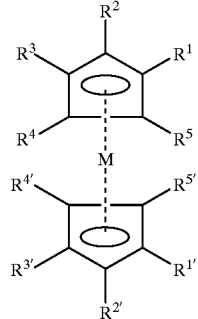

(I)

where
R¹ is a radical of the formula PL₂ where the L radicals can be identical or different and are alkyl, cycloalkyl or aryl,
R¹' is hydrogen, alkyl or a radical of the formula PL₂ where the L radicals have the abovementioned meaning,
R², R²', R³, R³', R⁴, R⁴', R⁵, R⁵' are, independently of one another, selected from hydrogen, cycloalkyl, aryl or alkyl, which can be interrupted by an oxygen atom or substituted by a radical of the formula NE¹E² where E¹ and E² can be identical or different and are alkyl, cycloalkyl or aryl, or in each case two of the substituents R², R³, R⁴, R⁵ and/or R²', R³', R⁴', R⁵' in adjacent positions can, together with the part of the cyclopentadienyl ring connecting them, be an aromatic or non-aromatic 5- to 7-membered carbocyclic or heterocyclic system which may have 1, 2 or 3 heteroatoms selected from O, N and S,
M is Fe, Co, Ni, Ru, Os, Rh, Mn, Cr or V,
or salts and mixtures thereof.
2. A process as claimed in claim 1, wherein a catalyst of the formula I where M is Fe is employed.
3. A process as claimed in claim 1, which comprises a catalyst of the formula I
wherein
R¹ is a radical of the formula PL₂ where the L radicals are phenyl,
R¹α is hydrogen or a radical of the formula PL₂ where the L radicals are phenyl, one of the substituents R², R²', R³, R³', R⁴, R⁴', R⁵ or R⁵' are, independently of one another, hydrogen, cycloalkyl, aryl or alkyl, which can be interrupted by an oxygen atom or substituted by a radical of the formula NE¹E² where E¹ and E² can be identical or different and are alkyl, cycloalkyl, aryl or in each case two of the substituents R², R²', R³, R³', R⁴, R⁴', R⁵ or R⁵' in adjacent positions can, together with the part of the cyclopentadienyl ring connecting them, be an aromatic or nonaromatic 5- to 7-membered carbocyclic or heterocyclic system which may have 1, 2 or 3 heteroatoms selected from O, N and S, is employed.

4. A process as claimed in claim 1, wherein a catalyst which has a ligand of the formula I and in addition at least one other ligand selected from halides, amines, carboxylates, acetylacetonate, aryl- or alkylsulfonates, hydride, CO, olefins, dienes, cycloolefins, nitriles, N-containing heterocycles, aromatic and heteroaromatic systems, ethers, $PF_3$ and monodentate, bidentate and multidentate phosphine, phosphinite, phosphonite and phosphite ligands is employed.

5. A process as claimed in claim 1, wherein the metallocene-phosphorus(III) ligand of the formula I is selected from 1,1'-bis(diphenylphosphino)ferrocene,
1,1'-bis(diisopropylphosphino)ferrocene or
1,1'-bis(dicyclohexylphosphino)ferrocene.

6. A process as claimed in claim 1, wherein a hydrocarbon mixture with a 1,3-butadiene content of at least 10% by volume is employed.

7. A process as claimed in claim 1, wherein a $C_4$ cut from petroleum processing is employed as 1,3-butadiene-containing hydrocarbon mixture.

8. A process as claimed in claim 1, wherein the hydrocyanation is carried out semicontinuously by a) charging a reactor with the hydrocarbon mixture, with or without part of the hydrogen cyanide and a catalyst which has been generated in situ where appropriate, with or without a solvent, b) reacting the mixture at elevated temperature under elevated pressure, with hydrogen cyanide being fed in at the rate of its consumption and c) completing the conversion by subsequent reaction, if required, followed by workup.

9. A process as claimed in claim 1, wherein the hydrocyanation is carried out batchwise with the total amount of hydrogen cyanide being present in stage a) in a process as claimed in claim 8.

10. A process as claimed in claim 1, wherein the hydrocyanation is carried out at from 0 to 200° C.

11. A process as claimed in claim 1, wherein the hydrocyanation is carried out under a pressure of from 1 to 200 bar.

12. A process as claimed in claim 11, wherein the conversion of hydrogen cyanide in the reaction is at least 95%.

13. A process as claimed in claim 1, wherein the resulting product mixture comprises isomeric pentenonitriles and methylbutenonitriles.

14. A process as claimed in claim 13, wherein the ratio of the amounts of 3-pentenonitrile to 2-methyl-3-butenonitrile is at least 5:1.

15. A process as claimed in claim 1, wherein the catalyst is employed, in addition to the hydrocyanation of 1,3-butadiene, also in the additional step of positional and double-bond isomerization of the hydrocarbon mixture and/or of the monoolefinic $C_5$ mononitriles.

16. A process for preparing adiponitrile, which comprises catalytically hydrocyanating a mixture of $C_5$ mononitriles prepared as claimed in claim 1.

17. A process as claimed in claim 16, wherein the hydrocyanation of 1,3-butadiene or of the 1,3-butadiene-containing hydrocarbon mixture to prepare adiponitrile takes place in one stage, without separate workup and isomerization of $C_5$ mononitriles.

18. A process for the hydrocyanation of olefins, wherein olefins are reacted with hydrogen cyanide in the presence of a catalyst comprising a ligand of the formula I, as defined in claim 1.

19. A process for the positional and double-bond isomerization of monoolefinic $C_5$ mononitriles, wherein the monoolefinic $C_5$ mononitriles are contacted with a catalyst comprising a ligand of the formula I, as defined in claim 1.

20. A process as claimed in claim 10, wherein the hydrocyanation is carried out at from 70 to 100° C.

21. A process as claimed in claim 11, wherein the hydrocyanation is carried out under a pressure of from 1 to 16 bar.

22. A process as claimed in claim 12, wherein the conversion of hydrogen cyanide in the reaction is at least 97%.

23. A process as claimed in claim 12, wherein the conversion of hydrogen cyanide in the reaction is at least 99%.

* * * * *

UNITED STATES PATENT AND TRADEMARK OFFICE
CERTIFICATE OF CORRECTION

PATENT NO. : 6,169,198 B1
DATED : January 2, 2001
INVENTOR(S) : Fischer et al.

Page 1 of 1

It is certified that error appears in the above-identified patent and that said Letters Patent is hereby corrected as shown below:

Column 5,
Line 33, "position αto" should be -- position α to --.
Line 47, "Co" should be -- CO --.
Line 48, "nitrites" should be -- nitriles --.

Column 11,
Line 9, "Chd4 cut" should be -- $C_4$ cut --.

Column 12, claim 3,
Line 58, "$R^1$ α is hydrogen" should be -- $R^1$ is hydrogen --.

Signed and Sealed this

Eleventh Day of September, 2001

*Attest:*

NICHOLAS P. GODICI
*Attesting Officer*   *Acting Director of the United States Patent and Trademark Office*